United States Patent
Kjær et al.

(10) Patent No.: US 6,596,154 B1
(45) Date of Patent: Jul. 22, 2003

(54) METHOD FOR REGULATING THE SENSITIVITY OF A MICROSENSOR, AND A MICROSENSOR THAT MAKES USE OF THIS METHOD

(75) Inventors: Thomas Kjær, Valby (DK); Lars Hauer Larsen, Hinnerup (DK)

(73) Assignee: Unisense Aps., Aarhus (DK)

( * ) Notice: Subject to any disclaimer, the term of this patent is extended or adjusted under 35 U.S.C. 154(b) by 0 days.

(21) Appl. No.: 09/623,161
(22) PCT Filed: Mar. 2, 1999
(86) PCT No.: PCT/DK99/00097
§ 371 (c)(1), (2), (4) Date: Aug. 25, 2000
(87) PCT Pub. No.: WO99/45376
PCT Pub. Date: Sep. 10, 1999

(30) Foreign Application Priority Data

Mar. 3, 1998 (DK) .............................................. 0285/98

(51) Int. Cl.[7] ..................... G01N 27/327; G01N 27/333
(52) U.S. Cl. ..................... 205/777.5; 778/789; 778/781; 204/403.01; 204/403.06; 204/431; 204/416
(58) Field of Search ..................... 204/403.01, 403.06, 204/431, 416, 419, 418; 205/777.5, 778, 780.5, 781, 789, 688, 701

(56) References Cited

PUBLICATIONS

Larsen et al. ("A Microscale NO3– Biosensor for Environmental Applications," Analytical Chemistry, vol. 69, No. 17, Sep. 1, 1997.*

* cited by examiner

Primary Examiner—Nam Nguyen
Assistant Examiner—Alex Noguerola
(74) Attorney, Agent, or Firm—Barneys & Thornburg

(57) ABSTRACT

The inventive microsensor and method for regulating the sensitivity primarily aims at measuring the nitrate concentration in a surrounding medium by use of a concept named "Migrational Sensitivity Control" (MSC). The sensitivity of the sensor is regulated by impressing an electrical potential difference or an electrical current between a surrounding medium, e.g. waste water, containing a primary substance to be measured, and a substance chamber inside the microsensor. The microsensor contains bacteria which metabolizes the primary substance into a secondary substance, the concentration of which is proportional to the conentration of the primary substance to be measured. By measuring the concentration of the secondary substance the concentration of the first substance can be found. By varying the impressed voltage or current, the sensitivity of the microsensor can be controlled.

15 Claims, 4 Drawing Sheets

Figure 1:
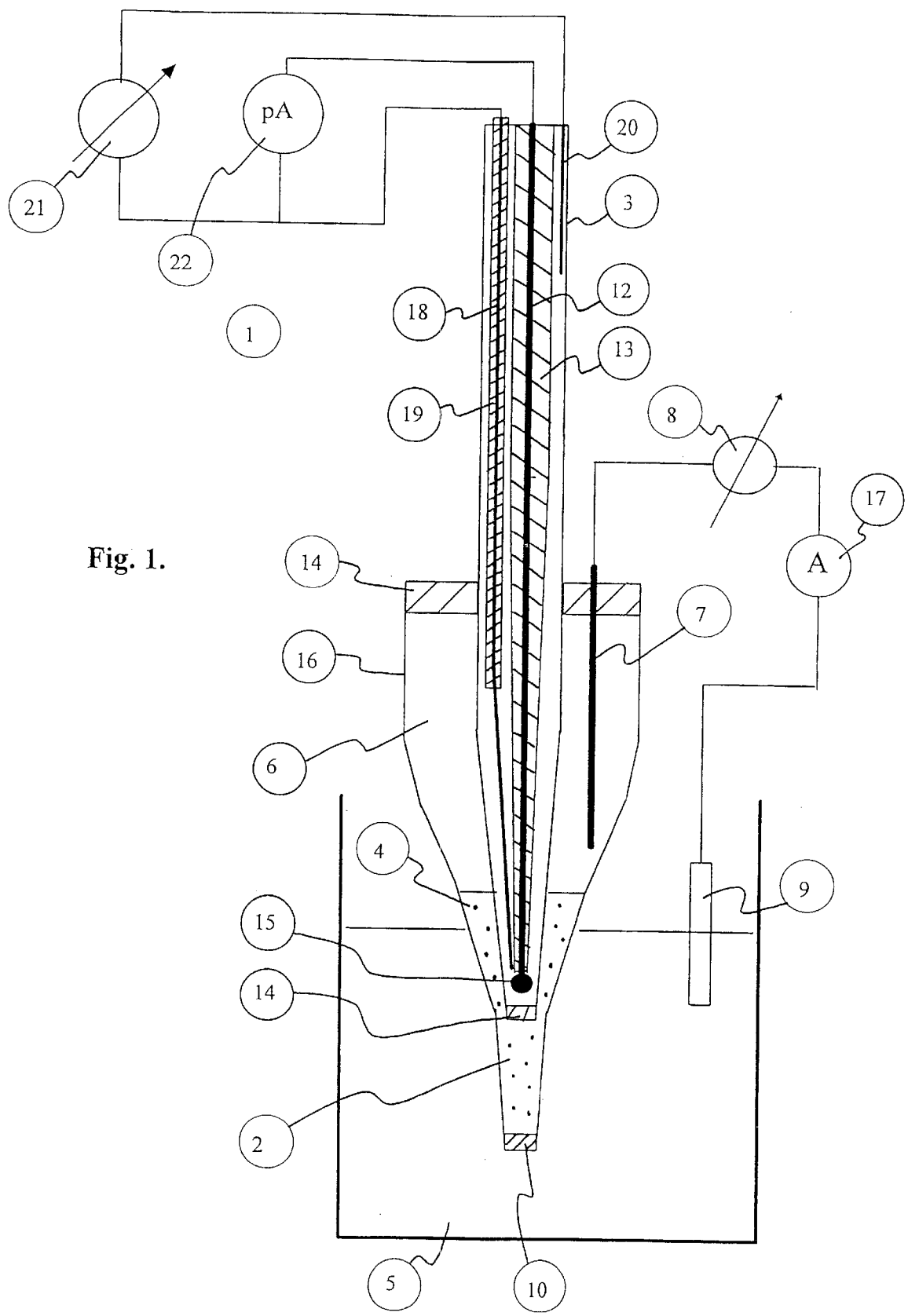

METHOD FOR REGULATING THE SENSITIVITY OF A MICROSENSOR, AND A MICROSENSOR THAT MAKES USE OF THIS METHOD

This application is the National Stage of International Application PCT/DK99/00097, filed Mar. 2, 1999.

TECHNICAL FIELD OF INVENTION

The invention relates to electro-chemical measuring equipment and to a method for measuring the concentration of electrically charged particles in a liquid. The invention in particular relates to a method and an apparatus (a microsensor) by means of which it is possible to determine the above mentioned concentration by measuring the concentration of a secondary substance, the concentration of which is proportional to the concentration of the said first mentioned particles (primary substance), as appears from the preamble of claim 1.

BACKGROUND OF THE INVENTION

A $NO_3^-$ microsensor based on immobilized nitrate reductase is described by E. Willner, E. Katz and N. Lapidot, 1992, "Bioelectroanalyzed reduction of nitrate utilizing polythiophene bipyridinium enzyme electrodes", Bioelectrochem. Bioenerg., 29, pp. 29–45. Here a negatively charged gold cathode receives electrons that originates from the reduction of $NO_3^-$ to $NO_2^-$, and the electrical connection between the cathode and enzymes are obtained through redox-active copolymers. The electron current from the cathode to a reference electrode was shown to be proportional with the $NO_3^-$ concentration in a buffer, and the electrode might be used to obtain a quantitative determination of $NO_3^-$ in aqueous solutions. However, it is not clear, whether this biosensor can work in natural surroundings with a variable chemical composition.

The international patent application PCT/DK96/00488 describes a microsensor primarily for on-line measurement of the methane concentration based on a bacterial conversion of methane when consuming oxygen, and measurement of the oxygen concentration. The invention enables measurement of the methane-concentration with a considerable spacious solution even in areas where steep concentration gradients occur. However, it is not possible to control the sensitivity during measurement of the methane concentration according to the invention.

The Japanese patent application No. 55072853 A describes a microsensor for measuring the concentration of ammonia in a given solution by means of bacterial conversion of ammonia with oxygen. The sensor consists of a thin bacteria layer placed on a suitable supporting element (a screen, filter a.o.) followed by a sensor for measurement of the oxygen concentration which in itself is a known technique. Also in this case, it is not possible to perform a calibration of the sensor sensitivity.

Contrary to the above systems U.S. Pat. No. 5,234,566 describes a biosensor consisting of a lipid diaphragm having at least one controlled ion channel, the electrical conductivity of which is dependent on the electrical potential difference over the diaphragm.

In principle it is, therefore, possible to calibrate this sensor by varying the applied potential difference. In this system there is no bacterial metabolism of a primary substance (the concentration of which is to be determined) to a secondary substance (the concentration of which can be measured by known techniques), as the patent only describes the conditions around the above mentioned diaphragm.

U.S. Pat. No. 5,474,660 describes a sensor for measurement of the ammonium ion concentration in a solution where the above mentioned sensor functions by measuring the concentration of ammonia. The conversion of ammonium ions into gaseous ammonia takes place by means of an electro-chemical generator having an electrode system which produces hydroxides in the area outside the sensor tip. This production of hydroixid ions is controlled by means of the above mentioned electrode system. There is no microbial participation in the measurement.

SUMMARY OF THE INVENTION

Microsensors have contributed with considerable knowledge about the decomposition of nitrogen in nature, but particularly $NO_3^-$ sensors have caused problems due to noise and unstability on the output signal, which is described by K. Jensen, N. P. Revsbech and L. P. Nielsen, 1993, "Microscale distribution of nitrofication activity in sediment determined with a shielded microsensor for nitrate", Appl. Environ. Microbiol. 59, pp. 3287–3296.

The present invention combines measurement of the concentration of a primary substance through bacterial metabolism to a secondary substance the concentration of which can be measured in a known way by means of a measuring electrode, with the ability of controlling (calibrating) from the outside the sensitivity when measuring the concentration of the primary substance. The present invention in particular—but not exclusively—describes a microsensor determined for an on-line measurement of the concentration of nitrate ions $NO_3^-$ at bacterial consumption of these whereby laughing gas ($NO_2^-$) is being produced. Measurement of the concentration of laughing gas is carried out according to a known technique, and it can be shown (see L. H. Larsen, T. Kjær, N. P. Revsbech (1997), "A Microscale $NO_3^-$-Biosensor for Environmental Applications", Analytical Chemistry, Vol. 96, No. 17, p. 3527–3531) that within a large measuring area proportionality exists between the concentration of nitrate ions and the concentration of laughing gas.

It is thus the aim of the invention to provide a method and at least one concrete microsensor that makes use of this method, in order to measure on-line continuously the concentration of a primary substance with electrically charged particles in a solution, in a way that the sensitivity of the above mentioned measurement can be varied whereby a more simple calibration of the microsensor can be carried out.

The invention essentially consists of the following three fundamental elements: 1) a measuring electrode to measure the concentration of a secondary substance in a known way where the above mentioned substance in the described embodiment is laughing gas ($N_2O^-$), 2) an area, hereinafter called "reaction chamber", containing bacteria that brings about a metabolism of a primary substance, the concentration of which is to be determined, to the above mentioned secondary substance, and where the above mentioned reaction chamber is placed on the boundary surface between the above mentioned measuring electrode and the medium containing the primary substance, the concentration of which is to be determined, and 3) a suitable electrode means capable of applying an electrical potential difference between the substance contained in the above mentioned reaction chamber and above mentioned surrounding medium, containing the particles, the concentration of which is to be determined, in such a way that through variation of the above mentioned electrical potential difference it will become possible to vary the sensitivity of the measurement of the above mentioned primary substance.

The advantages of the above mentioned invention are that it is possible to vary externally the sensitivity of the measurement of the concentration of the primary substance, hereby being able to adapt the sensitivity to the conditions that rule in the actual measuring situation. In particular one advantage is obtained, namely that in polarization of the potential in the reaction chamber with the same charge sign as the electrical charge of the particles to be measured, it is possible to determine the zero or idle current of the microsensor. Further, by applying to the reaction chamber a large electrical potential difference relative to the surrounding medium but with opposite charge sign relative to the electrically charged particles, the concentration of which is to be determined, it is possible to determine the maximum signal amplitude of the microsensor, that is exactly the concentration of the primary substance, whereafter there will no longer exist proportionality between the concentration of the primary and the secondary substance. A calibration curve for the sensor can thus be obtained by means of just one solution of the primary substance, the concentration of which has been determined by means of another method. In general the invention can be summarized as Migrational Sensitivity Control (MSC).

SHORT DESCRIPTION OF THE DRAWINGS

FIG. 1 Schematic illustration of the microsensor according to the invention

Figure 2:
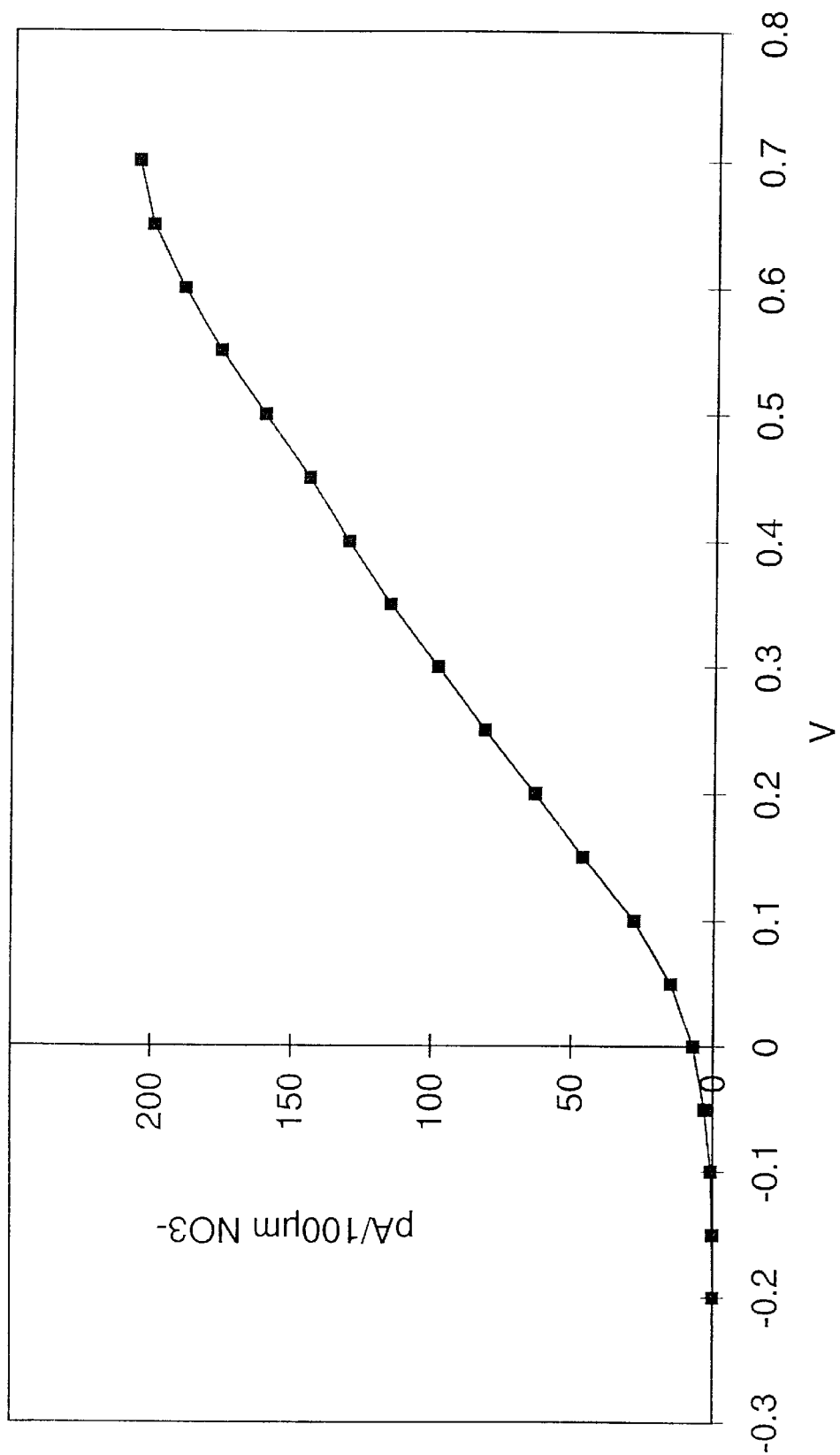
Figure 3:
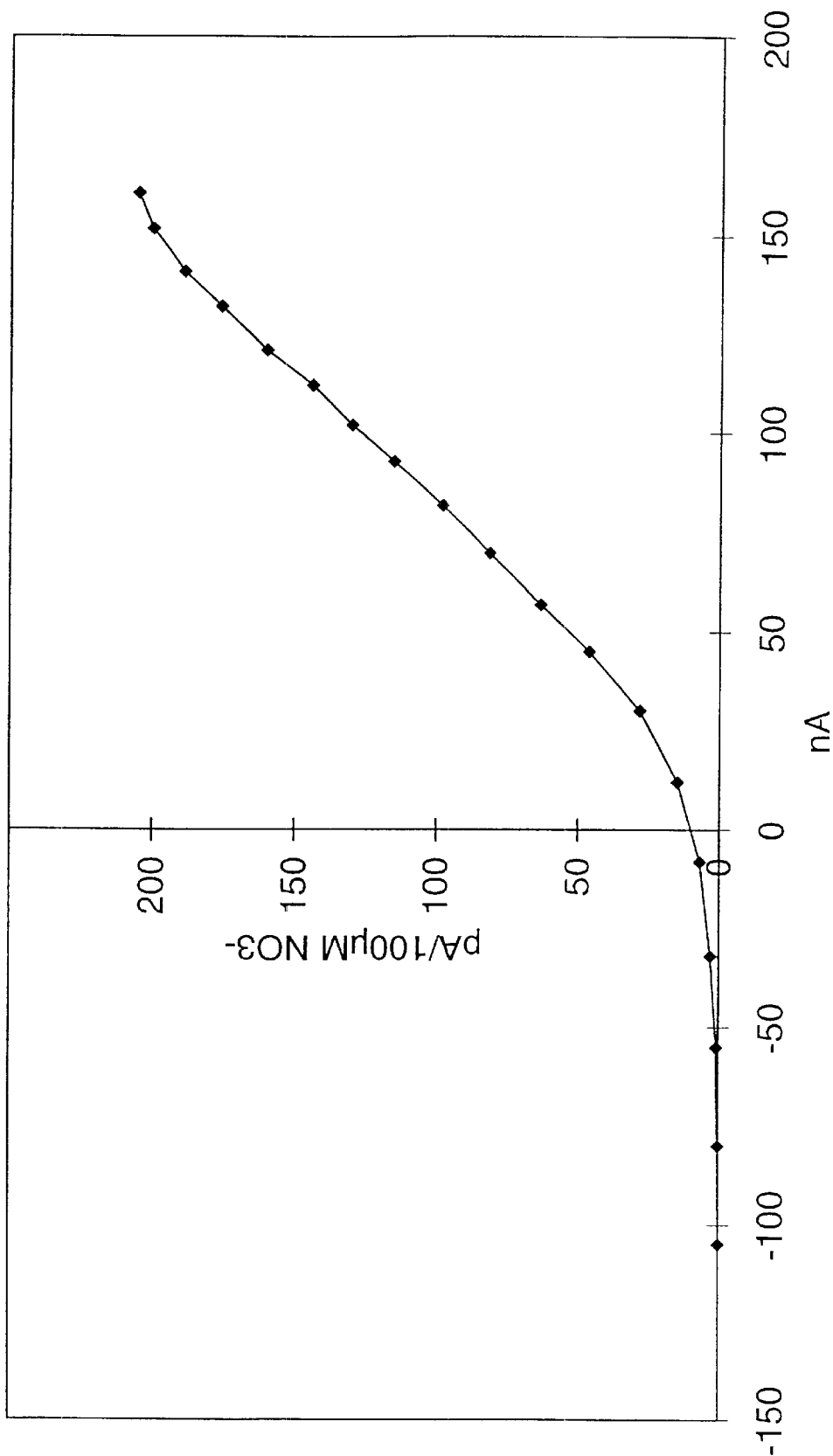
Figure 4:
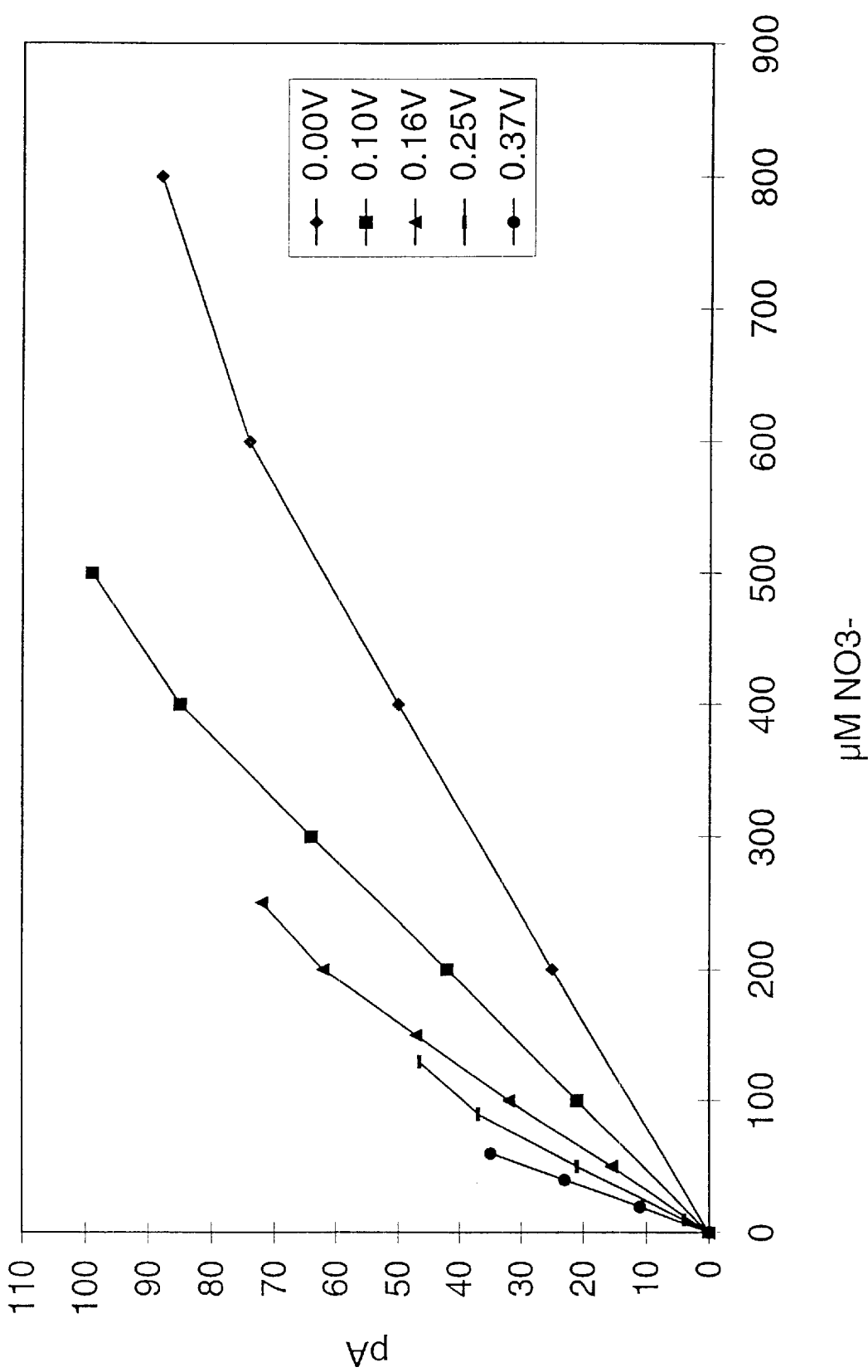

FIG. 2 The sensor signal as a function of the potential difference between the reaction chamber and the surrounding medium FIG. 3 The sensor signal as a function of the current between the reaction chamber and the surrounding medium FIG. 4 Calibration curves for a nitrate sensor according to the invention at different amounts of migrating ions

DETAILED DESCRIPTION OF THE INVENTION

Below is a description of a simple embodiment of the microsensor according to the invention. According to FIG. 1 it consists of an electrochemical laughing gas transducer (3) which according the description below for example consists of a silver electrode or a palladium electrode where the quantity of laughing gas per time unit reproduced on its cathode determines the signal amplitude of the nitrate ion sensor. Mathematically the quantity of laughing gas flowing to the cathode ($Flow_{N2O}$) can be described as follows:

$$Flow_{N2O} = (1/2) \cdot (A/L) \cdot C_{NO3^-} \cdot d_{NO3^-} \quad (1)$$

where $C_{NO3^-}$ is the concentration of nitrate outside the sensor tip, $d_{NO3^-}$ is the effective diffusion coefficient of nitrate in the reaction chamber and A/L is the ratio between the cross-sectional area and the length of the reaction chamber.

The laughing gas transducer 3 comprises a cathode 12 which over the main part of its length is surrounded by an coating 13 mainly consisting of gas. In the space between the gas coating and the outer wall of the transducer 3 a suitable electrolyte is placed. The transducer 3 is at the lower end delimited by a silicone diaphragm 14 through which the transducer 3 is connected with the reaction chamber 2. Immediately within the silicone diaphragm the uncoated tip 15 of the cathode is placed.

At the lower end of the above mentioned laughing gas transducer 3 is a substance chamber 6 surrounded by a impenetrable casing 16. Downward the substance chamber 6 ends up in a porous diaphragm 10 through which the nitrate sensor 1 is in communication with the surrounding medium 5, the nitrate concentration of which is to be measured. The lower part of the substance chamber 6 has around the tip of the laughing gas transducer 3 a reaction chamber 2 containing bacteria 4 which brings about a reduction of nitrate (primary substance) to laughing gas (secondary substance) by oxidizing at the same time carbon compounds from the substance chamber 6. The reduction process begins with the primary substance and ends with the secondary substance, but interimistic phases arise during the process, as nitrate turns into nitrite and then into nitric oxide (NO) and finally into laughing gas. The sensor is, therefore, also able to measure nitrite or nitric oxide.

Further the substance chamber 6 contains an electrode 7 the purpose of which is to apply an electrical potential difference between the substance chamber 6 and the surrounding medium 5, the nitrate concentration of which is to be measured. In order to apply the above mentioned potential difference, the surrounding medium 5 contains a reference electrode 9, and between this and the above mentioned electrode 7 a variable voltage supply 8 is inserted and, if required, a measuring device 17, for example an amperemeter.

The distance between the reference electrode 9 and the tip of the microsensor containing the porous diaphragm 10 is not critical and can be up to one meter. As the ion migration only happens between the reference electrode and the sensor tip, a minimum distance of 2–3 mm is necessary. Besides, it possible to built together the reference electrode 9 with the sensor 3, for example by placing the reference electrode 9 in a recess in the outer surface of the sensor house and guiding the reference electrode out in the area in front of the porous diaphragm 10. In this way a handy unit is obtained.

FIG. 1 is a schematic illustration of the ion pull-in (migration) mechanism which forms the basis of the above mentioned variation of the sensitivity of the microsensor 1 according to the invention. The flow of ions from the surrounding medium 5 into the microsensor 1 through the porous diaphragm 10 is a result of the chemical gradient (diffusion) over the diaphragm 10 as well as of the electrical gradient applied from outside. The electrical gradient is also called migration. These two gradients (the electrochemical gradient) thus form together the active gradient that the electrically charged particles are exposed to. These two gradients functions differently as a function of the distance, as the diffusion (that is the chemical gradient) is very effective over short distances whereas the electrical gradient is also effective over long distances. It is, therefore, possible to attract electrically charged particles in the surrounding medium 5 over long distances and thereby to measure very small concentrations. The resultant pull-in speed of ions into the sensor is a result of the chemical gradient and the applied electrical gradient and causes a net diffusion speed of ions into the sensor. Dependent on the sign of the electrical potential difference between the substance chamber 6 and the surrounding medium 5 or dependent of the (controlled) direction of current or amplitude, the total transport of electrically charged particles into the microsensor 1 will either increase relative to a merely chemical (diffusion) contribution or it will be impeded.

FIG. 2 illustrates the signal amplitude from the surrounding medium 5 containing 100 $\mu$M nitrate as a function of the applied electrical potential. It appears that by applying to the substance chamber 6 a negative polarization of –0.1V or less relative to the measuring medium the net transport of ions will be so small that no signal from the sensor can be registered. In the polarization interval of +0.1 to +0.6V the signal increases linearly as a function of the polarization. At increased positive polarization of the substance chamber 6 the signal size increases only little as the maximum nitrate reducing capacity of the reaction chamber 2 has been reached. The maximum linear area of the sensor is thus about 150 pA.

FIG. 3 illustrates the signal as a function of the current amplitude between the substance chamber 6 and the surrounding medium 5 with 100 $\mu$M nitrate. It can be seen that a current is flowing in the circuit even though no potential difference has been applied between the substance chamber 6 and the surrounding medium 5. This is caused by an electrical potential which is a result of different diffusion coefficients of the predominant positive and negative ions in the substance chamber 6.

FIG. 4 illustrates the calibration curves of a sensor at different levels of pull-in of ions. It appears from the figure that with the described type of pull-in it is possible to optimize the sensitivity of the sensor and/or the measuring area to a given situation. It can be seen that at an increasing polarization voltage the linear area of the sensor is reduced. This is due to the fact that the used bacteria 4 (origin Agrobacterium Radiobacter) are negatively charged and, consequently, are drawn away from the sensor tip which means that no metabolism of the primary substance nitrate will take place. The problem is pronounced at small concentrations of nitrate as the polarization voltage must be high. By using positive bacteria in stead they will move towards the sensor tip at measurement of low nitrate concentrations, but at reversal of the polarity carried out in order to reduce the nitrate sensitivity the bacteria will in stead migrate into the sensor. In general charged bacteria are not applicable at both low and high concentrations of nitrate. One solution is to make use of neutral bacteria, however, these may gradually become electrically charged in connection with changes in the surrounding medium. Another solution to the problem of bacteria-migration is to use a bacteria type that produces exo-polymers which retains the bacteria. The exo-polymers are segregated from the bacteria in form of mucilage in order that they can stick to the surface. It will also be possible to fixate the bacteria mutually by using calcium ions (Ca++) or another suitable chemical.

A considerable problem in connection with the application of a microsensor as described above is the ageing of the porous diaphragm 10, as an absolute voltage control of the ion transport will gradually lead to wrong results as the diaphragm becomes impermeable when it is ageing. Further, the resistance of the bacteria matrix will increase due to the presence of dead bacteria. This ageing problem can be completely eliminated through a current controlled ion pull-in. However, a sensor based on a current controlled ion transport will be sensitive towards changes in the ion concentration of the surrounding medium 5.

The resistance is also dependent on the diffusion coefficient of the ions that give rise to the electrical current through the porous diaphragm. The concentration of ions inside a typical sensor is much bigger than outside. From this follows, that the electrical current is caused primarily by ions coming from the inside of the sensor. The osmolyte used in connection with the results shown on FIGS. 2 and 3 is lithium chloride. A negative current is thus primarily the result of lithium ions moving from the inside to the outside. Chloride diffuses 1.5 to 2 times better than lithium. The resistance will, therefore, change dependent on whether the current into the sensor is negative or positive.

The ion pull-in shown on FIGS. 2 and 3 being a function of the applied potential difference or current leads to three things:

1. By polarizing the substance chamber 6 with the same sign as the electrically charged particles in the surrounding medium 5 it is possible to determine the zero current of the microsensor 1. This value is very important, for example in connection with waste water treatment plants where ventilation of the plant starts when the concentration of nitrate ions becomes zero.

2. By polarizing the substance chamber 6 with a reverse polarity relative to the electrically charged particles in the surrounding medium 5 a considerable number of these will move into the microsensor 1. In this way it is possible to determine the maximum signal amplitude that the microsensor 1 is able to provide (saturation point on FIGS. 2 and 3).

3. By controlling the applied electrical potential difference or current it is possible to optimize the sensitivity of the microsensor 1 regarding the actual surrounding medium 5.

The measuring electrode referred to above which measures the concentration of the secondary substance (for example laughing gas) has until now worked by means of a silver or platinum cathode. However, other researchers (see A. Kudo, A. Mine: "Electrocatalysis for $N_2O^-$ reduction on metal electrodes", Journal of Electroanalytical Chemistry, 1996, Vol. 408, p. 267–269) have proved that other metals can also be catalytically active as regards reduction of laughing gas. It has been shown that by using a palladium electrode in stead of a silver electrode the zero voltage can be reduced by 90–95%.

Besides, a palladium electrode typically means a doubble signal level at a given laughing gas concentration compared with a silver electrode. In a preferred embodiment of the laughing gas electrode as shown schematically on FIG. 1, a platinum wire with a palladium surface 18, which over about $^2/_3$ of its length has an isolating coating 19, is placed along the side of the measuring electrode (12,13,15), and the platinum wire is polarized with the same voltage as the measuring cathode 12. The advantage obtained hereby is that the electrolyte is reduced and thereby also a reduction of the zero current on the measuring cathode is achieved. Another important function of this metal wire having a palladium surface is that it catches substances which would cause a contamination on the measuring cathode and thereby destroy its catalytic activity. Without this electrolytic cleaning the life of the palladium electrode would be short.

By means of the variable voltage supply 21 a suitable potential difference between the measuring cathode 12, respectively the palladium electrode 18 and the surrounding electrolyte where the other reference electrode 20 is placed. By means of the pico-amperemeter 22 the concentration of laughing gas and thereby the concentration of nitrate ion can be determined.

What is claimed is:
1. A method for measuring the concentration of a primary substance consisting of electrically charged particles in a fluid medium, the method comprising
providing a fluid medium comprising a primary substance consisting of electrically charged particles;
providing within said fluid medium an area containing bacteria that converts said primary substance into a secondary substance;
allowing the primary substance to diffuse into said area; and
controlling the net diffusion rate of said electrically charged particles from the fluid medium into said area by applying an electrical potential difference or a predetermined electrical current between said area containing bacteria and the surrounding fluid medium.

2. Method according to claim 1 including varying the sensitivity of the measurement of the primary substance of the fluid medium through the control of the net diffusion rate.

3. Method according to claim 1 in which the bacteria consist of denitrifying bacteria which cause a conversion of nitrate ions ($NO_3$) into laughing gas ($N_2O$) so that through determining the concentration of $N_2O$ it is possible to determine the concentration of nitrate ions in the fluid medium.

4. A microsensor for measuring the concentration of electrically charged particles in a fluid medium, the microsensor comprising a transducer for measuring a secondary substance so that the concentration of a primary substance can be determined, wherein the transducer is located in a casing that has a porous diaphragm and the transducer has a lowest end situated in a surrounding substance chamber, and wherein the substance chamber includes a reaction chamber proximate said lowest end and contains bacteria that can metabolize a primary substance contained in the fluid medium into a secondary substance, the substance chamber has a porous diaphragm in the reaction chamber in communication with the fluid medium, and the substance chamber contains a first electrode situated at a given distance from one side of the diaphragm, the first electrode being connected to a voltage supply such that the first electrode is impressed with an electrical potential relative to a reference electrode located in the fluid medium, wherein a measuring device is located between the first electrode and the reference electrode.

5. Microsensor according to claim 4 in which the voltage supply can vary the electrical potential in a way so that it is possible to vary the sensitivity of the microsensor with regard to concentration of the secondary substance.

6. Microsensor according to claim 4 including means to keep the sensitivity of the microsensor with regard to the secondary substance constant in that the current between the substance chamber and the surrounding medium is constant, but to vary the impressed electrical potential.

7. Microsensor according to claim 4 in which the bacteria in the reaction chamber are fixated.

8. Microsensor according to claim 7 in which the bacteria are fixated by using bacteria that have a neutral electrical charge.

9. Mircosensor according to claim 7 in which the bacteria are fixated by using exo-polymer producing bacteria.

10. Microsensor according to claim 7 which bacteria are fixated by binding chemically the bacteria.

11. Microsensor according to claim 4 in which the bacteria in the reaction chamber is denitrifying bacteria which cause a metabolism of nitrate ions ($NO_3$)comprising the primary substance into the secondary substance comprising laughing gas ($N_2O$), and the microsensor determines the concentration of nitrate ions in the fluid medium by means of the transducer which measures the concentration of laughing gas produced during the denitrifying bacteria's consumption of nitrate ions coming from the fluid medium.

12. Microsensor according to claim 11, in which the transducer for measurement of the concentration of laughing gas contains a silver electrode.

13. Microsensor according to claim 11, in which the transducer for measurement of the concentration of laughing gas contains a palladium electrode as a measuring cathode.

14. Microsensor according to claim 11, in which the transducer for measurement of the concentration of laughing gas contains a metal filament with a palladium surface.

15. Microsensor according to claim 14, in which the metal filament with the palladium surface is polarized with the same potential as the transducer for measurement of the concentration of laughing gas.

* * * * *